US011180990B2

(12) United States Patent
Indo et al.

(10) Patent No.: US 11,180,990 B2
(45) Date of Patent: Nov. 23, 2021

(54) FLOWLINE SATURATION PRESSURE MEASUREMENT

(71) Applicant: Schlumberger Technology Corporation, Sugar Land, TX (US)

(72) Inventors: Kentaro Indo, Sugar Land, TX (US); Maxim Yushko, Houston, TX (US); Tudor Ioan Palaghita, Houston, TX (US); Zeynep Alpman, Houston, TX (US); Alexis Petit, Dhahran (SA); Julian Pop, Houston, TX (US); Sepand Ossia, Houston, TX (US); Tullio Moscato, Paris (FR)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 0 days.

(21) Appl. No.: 16/908,149

(22) Filed: Jun. 22, 2020

(65) Prior Publication Data
US 2020/0325774 A1 Oct. 15, 2020

Related U.S. Application Data

(62) Division of application No. 15/623,440, filed on Jun. 15, 2017, now Pat. No. 10,689,979.

(60) Provisional application No. 62/350,943, filed on Jun. 16, 2016.

(51) Int. Cl.
*E21B 49/08* (2006.01)
*E21B 47/06* (2012.01)
*G01N 33/28* (2006.01)

(52) U.S. Cl.
CPC .............. *E21B 49/08* (2013.01); *E21B 47/06* (2013.01); *G01N 33/28* (2013.01)

(58) Field of Classification Search
CPC ........ E21B 49/08; E21B 47/06; E21B 49/081; E21B 49/10; E21B 49/0875; G01N 33/28
See application file for complete search history.

(56) References Cited

U.S. PATENT DOCUMENTS

| 5,329,811 | A | 7/1994 | Schultz et al. |
|---|---|---|---|
| 5,473,939 | A | 12/1995 | Leder et al. |
| 6,334,489 | B1 | 1/2002 | Shwe et al. |
| 7,222,524 | B2 | 5/2007 | Shammai |
| 7,346,460 | B2 | 3/2008 | DiFoggio et al. |
| 7,461,547 | B2 | 12/2008 | Terabayashi et al. |
| 7,774,141 | B2 | 8/2010 | Li |
| 8,616,282 | B2 | 12/2013 | Moscato et al. |
| 8,778,835 | B2 | 7/2014 | Hungenberg et al. |
| 9,536,758 | B1 | 1/2017 | Deo |
| 2004/0231408 | A1 | 11/2004 | Shammai |
| 2009/0188259 | A1 | 7/2009 | Colja et al. |
| 2011/0315375 | A1 | 12/2011 | Moscato et al. |
| 2013/0068453 | A1 | 3/2013 | Al-Ajaji et al. |

(Continued)

OTHER PUBLICATIONS

Artic TEC Technologies (Dortmund, Germany, arctictec.com).
(Continued)

*Primary Examiner* — Taras P Bemko

(57) ABSTRACT

A method for sampling a downhole formation fluid includes pumping formation fluid into the flowline of a downhole sampling tool, measuring a saturation pressure of the formation fluid in the flowline while pumping, and adjusting the pumping rate such that the fluid pressure in the flowline remains within a predetermined threshold above the measured saturation pressure.

8 Claims, 7 Drawing Sheets

(56) References Cited

U.S. PATENT DOCUMENTS

| | | |
|---|---|---|
| 2013/0219997 A1 | 8/2013 | Sullivan et al. |
| 2014/0096955 A1 | 4/2014 | Indo et al. |
| 2014/0268156 A1 | 9/2014 | Smythe et al. |
| 2017/0045591 A1 | 2/2017 | Jelezko et al. |
| 2017/0362936 A1 | 12/2017 | Indo et al. |
| 2018/0051553 A1 | 2/2018 | Indo et al. |

OTHER PUBLICATIONS

Wikipedia page of TE cooling technique: https://en.wikipedia.org/wiki/Thermoelectric_cooling.

Office Action issued in U.S. Appl. No. 15/678,141 dated Nov. 18, 2019, 11 pages.

FLOWLINE SATURATION PRESSURE MEASUREMENT

CROSS REFERENCE TO RELATED APPLICATIONS

This application is a Divisional Application of U.S. patent application Ser. No. 15/623,440, filed Jun. 15, 2017 entitled Flowline Saturation Pressure Management, now U.S. Pat. No. 10,689,979, which claims the benefit of, and priority to, U.S. Provisional Patent Application No. 62/350,943, filed Jun. 16, 2016 and titled "Flowline Saturation Pressure Measurement." The foregoing applications are incorporated herein by this reference in their entirety.

FIELD OF THE INVENTION

Disclosed embodiments relate generally to sampling subterranean formation fluids and more specifically to a method and apparatus for measuring a saturation pressure of fluid in the flowline of a downhole sampling tool.

BACKGROUND INFORMATION

In order to successfully exploit subterranean hydrocarbon reserves, information about the subsurface formations and formation fluids intercepted by a wellbore is generally required. This information may be obtained via sampling formation fluids during various drilling and completion operations. The fluid may be collected and analyzed, for example, to ascertain the composition and producibility of hydrocarbon fluid reservoirs.

In order to obtain a reliable characterization of the reservoir fluid, drilling fluid filtrate contamination is desirably minimized, for example, via pumping fluid overboard until contamination levels reach an acceptably low level. Such a process can be time consuming as it sometimes requires pumping hundreds of liters of fluid overboard. Increasing the flow rate can be problematic as pumping too rapidly may reduce the flowline pressure below the saturation pressure of the fluid and thereby result in gas bubble formation. Such bubble formation can in turn decrease pumping efficiency and may further degrade optical spectroscopy measurements used to determine fluid contamination.

There is a need in the art for a method and apparatus for pumping formation fluid as rapidly as possible without drawing the flowline pressure below the saturation pressure of the fluid.

SUMMARY

A method for sampling a downhole formation fluid is disclosed. The method includes pumping formation fluid into the flowline of a downhole sampling tool, measuring a saturation pressure of the formation fluid in the flowline while pumping, and adjusting the pumping rate such that the fluid pressure in the flowline remains within a predetermined threshold above the measured saturation pressure. The saturation pressure may be measured in the flowline, for example, by heating formation fluid in the flowline while pumping, estimating a temperature of the fluid in the flowline while heating, evaluating the temperature estimates to determine a temperature indicative of bubble formation in the flowline, and processing a flowline pressure, a reference temperature, the temperature indicative of bubble formation, and a formation fluid model to compute the saturation pressure of the formation fluid at the reference temperature.

A downhole formation fluid sampling tool includes a fluid flowline deployed between a fluid inlet probe and a pump (i.e., upstream of the pump) and a bubble sensor deployed in the fluid flowline. The bubble sensor includes a heating element and a temperature sensor deployed on a common substrate (such as a diamond substrate). The sampling tool may further include a controller configured to implement the above described method.

The disclosed embodiments may provide various technical advantages. For example, disclosed embodiments may improve the pumping speed of formation fluid sampling operations while maintaining the flowline pressure below the saturation pressure of the formation fluid. The disclosed embodiments may further enable substantially continuous measurements of the saturation pressure in the flowline and therefore provide for rapid evaluation and adjustment of fluid sampling pumping rates.

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF THE DRAWINGS

For a more complete understanding of the disclosed subject matter, and advantages thereof, reference is now made to the following descriptions taken in conjunction with the accompanying drawings, in which.

DETAILED DESCRIPTION

Figure 1:
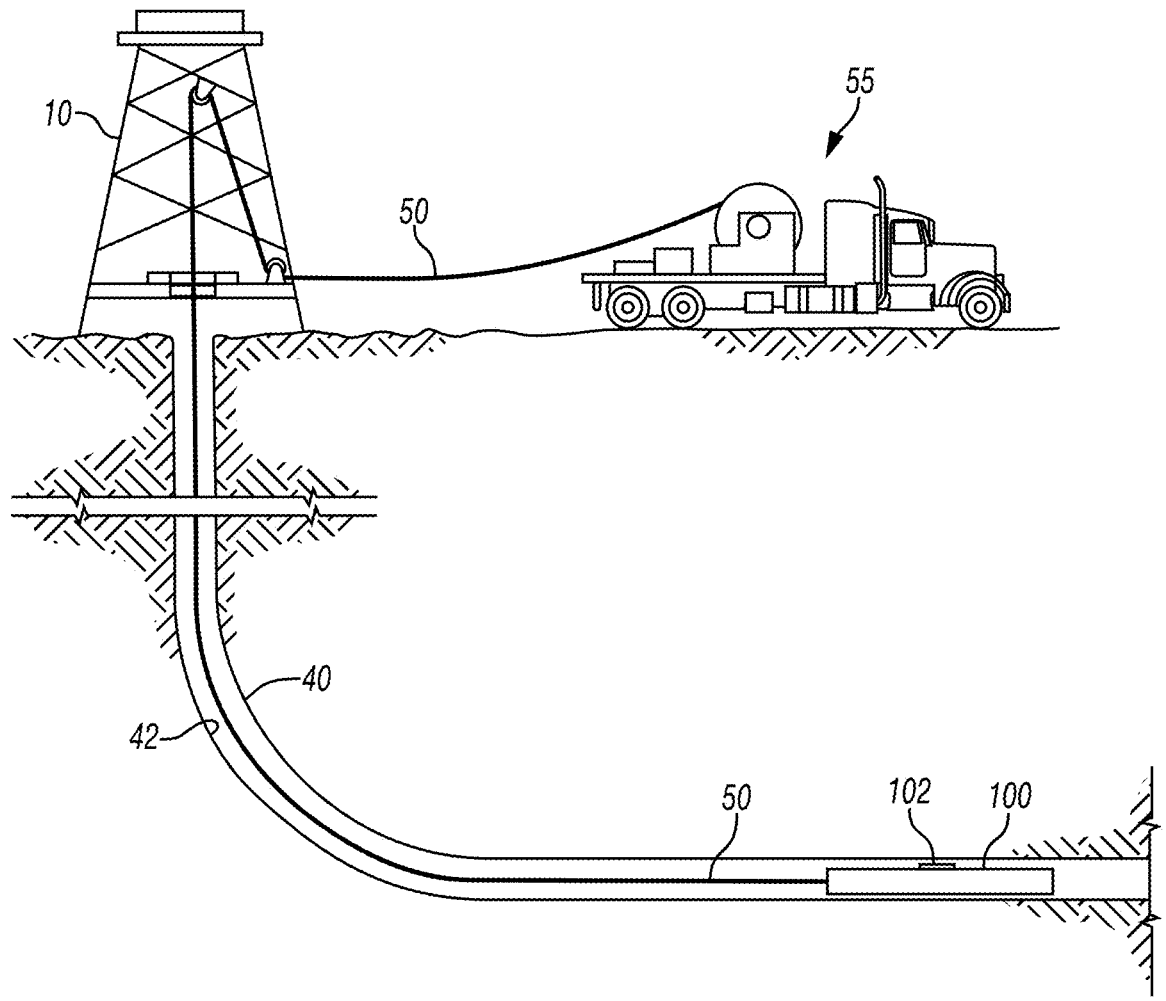
FIG. 1 depicts one example of a drilling rig on which disclosed sampling tool and method embodiments may be utilized.

FIG. 1 depicts a drilling rig 10 suitable for employing certain downhole tool and method embodiments disclosed herein. In the depiction, a rig 10 is positioned over (or in the vicinity of) a subterranean oil or gas formation (not shown). The rig may include, for example, a derrick and a hoisting apparatus for lowering and raising various components into and out of the wellbore 40. A downhole sampling tool 100 is deployed in the wellbore 40. The sampling tool 100 may be connected to the surface, for example, via a wireline cable 50 which may in turn be coupled to a wireline truck 55.

During a wireline operation, for example, sampling tool 100 may be lowered into the wellbore 40. In a highly deviated borehole, the sampling tool 100 may alternatively or additionally be driven or drawn into the borehole, for example, using a downhole tractor or other conveyance means. The disclosed embodiments are not limited in this regard. For example, sampling tool 100 may also be conveyed into the borehole 40 using coiled tubing or drill pipe conveyance methodologies. The sampling tool 100 may alternatively be deployed in a drill string for us in a "while-drilling" sampling operation.

The example sampling tool 100 described herein may be used to obtain formation fluid samples from a subterranean formation. The sampling tool 100 may include a probe assembly 102 for establishing fluid communication between the sampling tool 100 and the subsurface formation. During a sampling operation, the probe 102 may be extended into contact with the borehole wall 42 (e.g., through a mud cake/filtrate layer). Formation fluid samples may enter the sampling tool 100 through the probe assembly 102 (e.g., via pumping or via formation pressure).

While the disclosed embodiments are not limited in this regard, the probe assembly 102 may include a probe mounted in a frame (the individual probe assembly components are not shown). The frame may be configured to extend and retract radially outward and inward with respect to the sampling tool body. Moreover, the probe may be configured to extend and retract radially outward and inward with respect to the frame. Such extension and retraction may be initiated via an uphole or downhole controller. Extension of the frame into contact with the borehole wall 42 may further support the sampling tool in the borehole as well as position the probe adjacent the borehole wall.

While FIG. 1 depicts a wireline sampling tool 100, it will be understood that the disclosed embodiments are not so limited. For example, as stated above, sampling tool 100 may include a drilling tool such as a measurement while drilling or logging while drilling tool configured for deployment on a drill string. The disclosed embodiments are expressly not limited to wireline embodiments.

Figure 2:
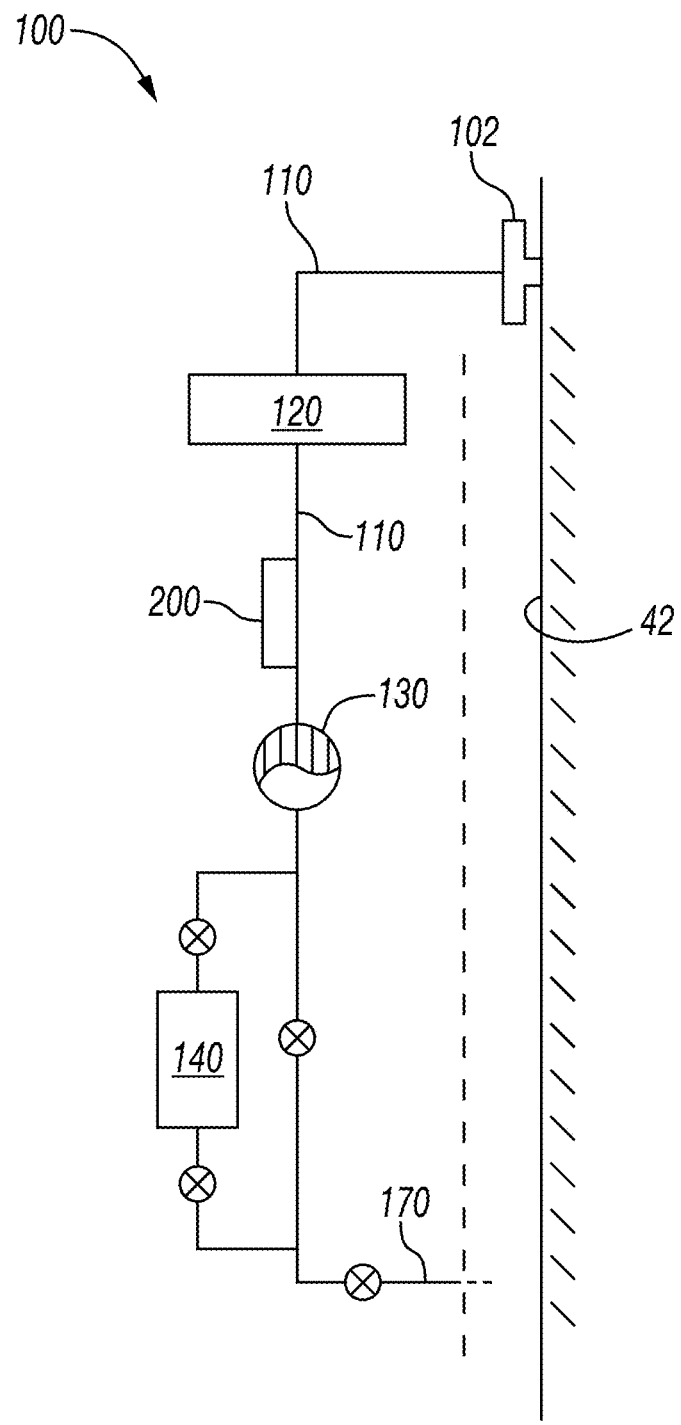
FIG. 2 depicts a downhole sampling tool including a schematic fluid flow circuit diagram.

FIG. 2 further depicts sampling tool 100 including a schematic fluid flow circuit diagram. As described above with respect to FIG. 1, the probe 102 is depicted as being in contact with the borehole wall 42 for obtaining a formation fluid sample. The probe 102 is in fluid communication with a primary flow line 110, which is in further communication with a bubble sensor 200, a fluid analysis module 120, and a pump 130. A sample vessel 140 is also in fluid communication with the primary flow line 110 and may be configured to receive a formation fluid sample. Sampling tool 100 further includes a fluid outlet line 170 configured for discharging unwanted formation fluid into the annulus or into the subterranean formation.

Fluid analysis module 120 may include substantially any suitable fluid analysis sensors and/or instrumentation, for example, including chemical sensors, optical fluid analyzers, optical spectrometers, nuclear magnetic resonance devices, a conductivity sensor, a temperature sensor, a pressure sensor. More generally, module 120 may include substantially any suitable device that yields information relating to the composition of the formation fluid such as the thermodynamic properties of the fluid, conductivity, density, viscosity, pressure, temperature, and phase composition (e.g., liquid versus gas composition or the gas content) of the fluid. While not depicted, it will be understood that fluid analysis sensors may alternatively and/or additionally be deployed on the downstream side of the pump 130, for example, to sense fluid property changes that may be induced via pumping.

Substantially any suitable sample vessel 140 may be utilized. The vessel may optionally include a piston that defines first and second chambers (not shown) within the vessel. As described in more detail below, the bubble sensor 200 may include a diamond substrate having at least one heating element and at least one temperature sensor deployed thereon. The bubble sensor 200 is preferably deployed on the upstream side of the pump 130 as depicted.

Figure 3:
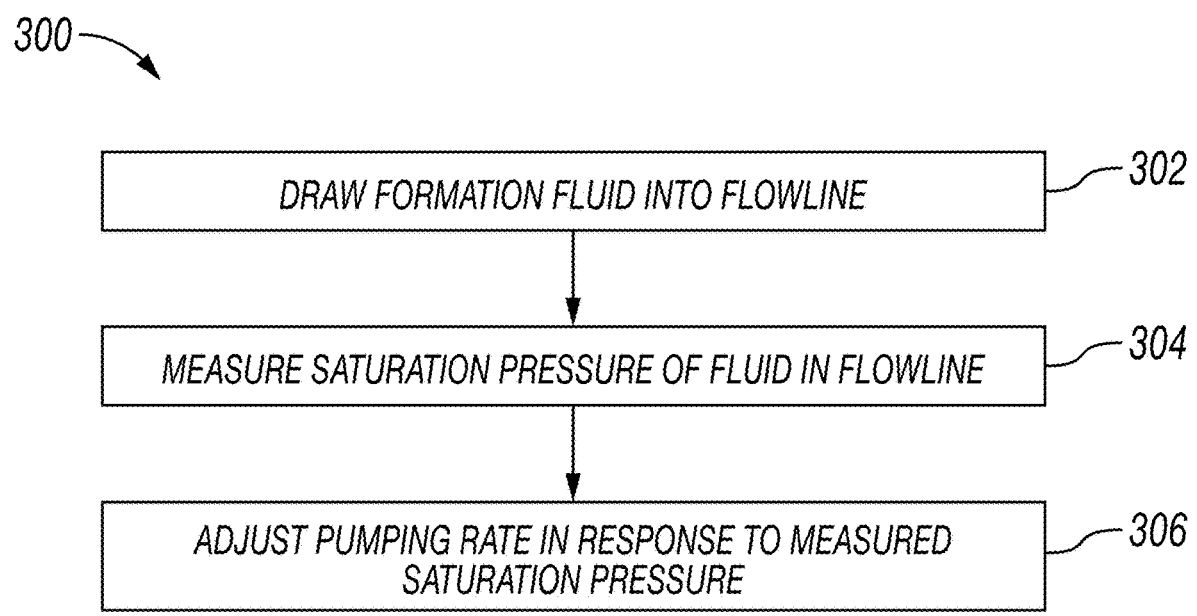
FIG. 3 depicts a flow chart of one disclosed method embodiment.

FIG. 3 depicts a flow chart of one disclosed method embodiment 300 for obtaining a formation fluid sample. At 302, formation fluid is drawn into the flowline of a downhole sampling tool (e.g., flowline 110 of sampling tool 100 depicted on FIGS. 1 and 2). While drawing/pumping fluid 302, the saturation pressure of the fluid in the flowline may be measured at 304 using a bubble sensor (e.g., bubble sensor 200) deployed on the flowline 310. The measurements may optionally be made substantially continuously, for example, at a measurement rate in a range from about 1 measurement per minute to about 1 measurement per second. The pumping rate may be adjusted at 306 in response to the saturation pressure value(s) measured at 304. The pumping rate is preferably adjusted such that the pressure in the flowline remains within a predetermined threshold above the measured saturation pressure.

As described above in the Background Section of this disclosure, sampled formation fluid is commonly discharged (e.g., via discharge port 170) until contamination levels (e.g., as measured using fluid analysis module 120) decrease below a predetermined acceptable level. Such contamination removal procedures commonly require a large volume of formation fluid to be pumped and discharged, which can be time consuming and expensive. It is therefore generally desirable to pump the formation fluid as rapidly as possible. However, increasing the pumping rate draws down the fluid pressure in the flowline upstream of the pump (e.g., upstream of pump 130 in FIG. 2), which may in turn cause gas bubbles to form if the pressure in the flowline drops below the saturation pressure of the fluid.

The emergence of gas bubbles is generally undesirable for a number of reasons. For example, formation fluid containing gas bubbles may not be representative of the original virgin fluid if the liberated gas is not captured with the liquid from which it originated. Moreover, the presence of gas bubbles may change the compressibility of the fluid and thereby reduce pumping efficiency. The presence of gas bubbles may also degrade the reliability of optical spectroscopy measurements used to monitor fluid contamination due to scattering.

Method 300 is intended to optimize the pumping speed such that a low contamination formation fluid sample may be obtained in a timely manner without drawing the flowline pressure below the saturation pressure of the fluid.

Figure 4:
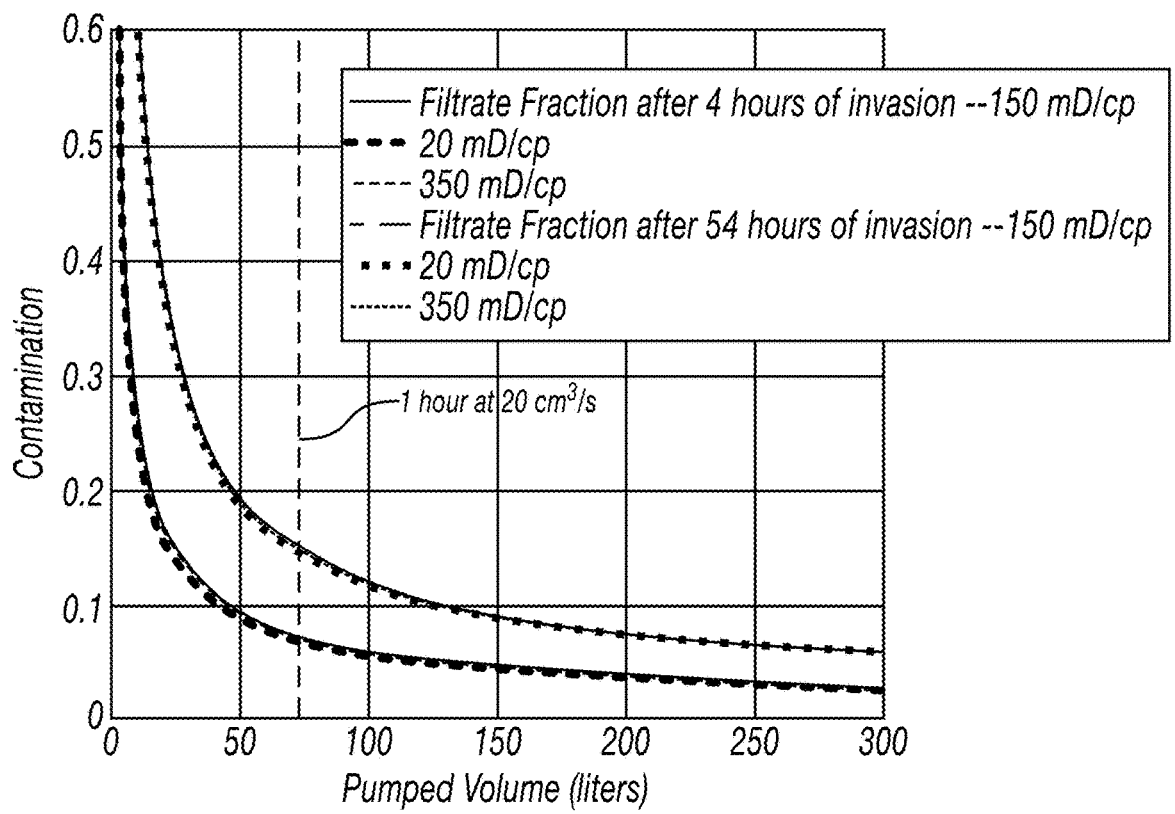
FIG. 4 depicts a plot of formation fluid contamination level versus pumped fluid volume during a sampling operation.

FIG. 4 depicts a plot of formation fluid contamination level (as a volume fraction) versus pumped volume of fluid during a sampling operation. Contamination levels are known to decrease approximately exponentially with pumped volume independent of the pumping speed (flowrate) and mobility of the fluid. Increased pumping is generally required with increasing invasion (note that contamination levels are significantly higher after 54 hours of invasion as compared to 4 hours of invasion).

Figure 5:
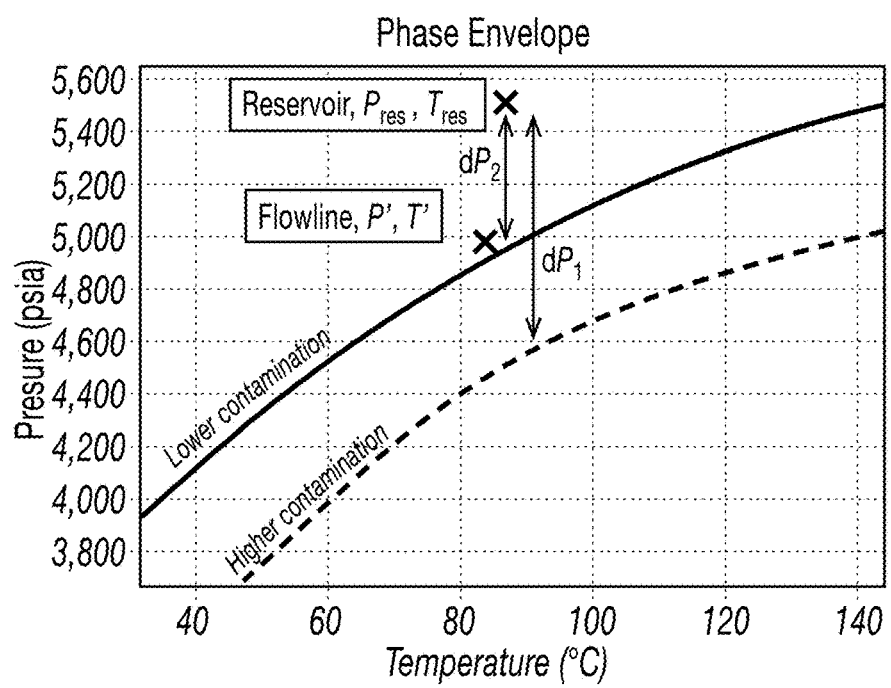
FIG. 5 depicts a portion of a pressure versus temperature phase envelope of an example crude oil sample.

FIG. 5 depicts a portion of a pressure versus temperature phase envelope of an example crude oil sample. As depicted, the saturation pressure (also referred to in the art as the bubble point for an oil or the dew point for a retrograde gas) depends on temperature and the contamination level of the fluid. The solid line indicates the phase boundary of the crude oil having a relatively low contamination level, whereas the dashed line indicates the saturation pressure of crude oil having a relatively high contamination level. For crude oil samples, the saturation pressure tends to be inversely related to the contamination level (i.e., decreasing with increasing contamination and increasing with decreasing contamination as depicted).

As described above it is desirable to maintain the flowline pressure above the saturation pressure to ensure a single phase fluid in the flowline (i.e., with no gaseous components). Initially, the pumping speed (the flow rate) may be high since the contamination level is initially high and thereby allows for a higher drawdown pressure $dP_1$ between the reservoir pressure and the saturation pressure. As pumping progresses and the contamination level decreases (e.g., as depicted on FIG. 4), it may be necessary to decrease the pumping speed to reduce the drawdown pressure (e.g., to $dP_2$) and avoid bubble formation. During a conventional sampling operation, the saturation pressure of the flowline fluid is generally unknown and continuously changing as contamination decreases. Moreover, as depicted on FIG. 4, the contamination levels may initially decrease very rapidly (e.g., exponentially). Real time, rapid saturation pressure measurements at 304 may enable the pumping rate to be continually adjusted and optimized at 306 such that a maximum pumping rate is achieved without causing the flowline pressure to drop below the saturation pressure.

Figure 6:
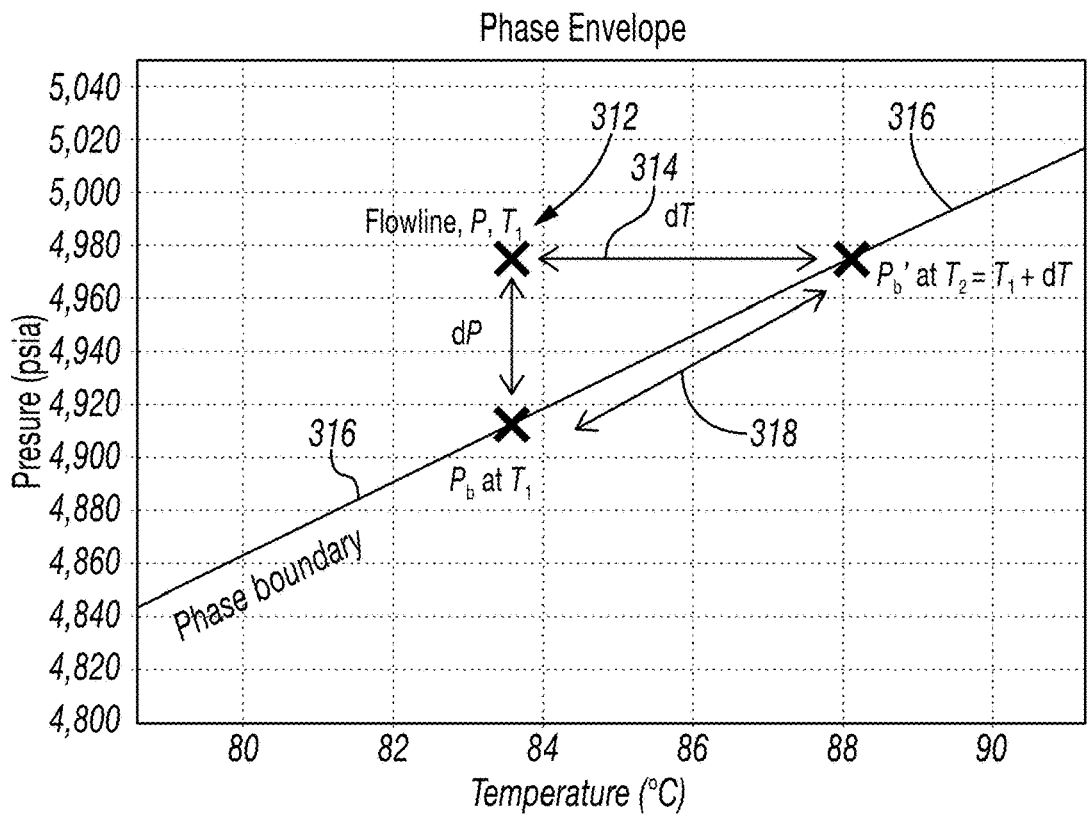
FIG. 6 plots a portion of the pressure-temperature phase envelope of an example crude oil sample and further illustrates one disclosed method embodiment.

Measurement of the saturation pressure of the formation fluid at 304 in FIG. 3 is described in more detail with respect to FIG. 6 which plots a portion of the pressure-temperature phase envelope of an example crude oil sample. The temperature $T=T_1$ and pressure P of the flowline fluid is depicted at 312. These parameters may be measured while pumping, for example, using reference temperature and pressure sensors deployed in fluid analysis module or elsewhere in the flowline. The saturation pressure $P_b$ of the formation fluid may be measured at 304, for example, by (i) locally heating the flowline fluid (e.g., using the heating element in the bubble sensor 200) until bubbles are formed, (ii) determining a temperature indicative of bubble formation, e.g., the temperature $T_2=T_1+\Delta T$ at which the saturation pressure $P'_b$ is equal to the flowline pressure P (i.e., such that $P'_b=P$ at $T_2$) and (iii) processing $P'_b$ and $T_2$ in combination with a fluid model to compute the unknown saturation pressure $P_b$ at temperature $T_1$.

With continued reference to FIG. 6, local heating of the flowline fluid is depicted at 314. Note that the flowline fluid may be heated at 314 until the temperature crosses (or reaches) the phase boundary 316 at which point bubble formation may be observed. The temperature $T_2=T_1+\Delta T$ at which bubbles form is the temperature at which the phase boundary intersects the flowline fluid pressure P (i.e., when the saturation pressure $P'_b$ is equal to the flowline fluid pressure P) and may be measured using the temperature sensor in the bubble sensor. The unknown saturation pressure $P_b$ of the flowline fluid at the flowline temperature $T_1$ may then be computed at 318 via processing $P'_b$ and $T_2$ in combination with a fluid model.

Various formation fluid models are known in the art. For example, in one embodiment, the phase boundary of crude oils may be described mathematically using an empirical linear regression model including second order terms, for example, as follows:

$$f(T, \{x_i\}) = a_T T + b_T T^2 + \sum_i a_i x_i + \sum_i \sum_{i \leq j} b_{ij} x_i x_j \quad (1)$$

where f (•) represents an estimated saturation pressure as a function of temperature T and fluid compositional inputs $\{x_i\}$ and $a_i$ and $b_{ij}$ represent coefficients which are calibrated against a fluid library, where i,j $\in CO_2$, $C_1$, $C_2$, $C_3$, $C_4$, $C_5$, $C_{6+}$ (with $C_1$, $C_2$ . . . representing methane, ethane, etc.).

The difference in saturation pressure dP between the first and second temperatures $T_1$ and $T_2$ may be derived from Equation 1, for example, as follows:

$$dP(T_1,T_2)=f(T_2,\{x_i\})-f(T_1,\{x_i\})=a_T dT+b_T[2T_1 dT+dT^2] \quad (2)$$

where $dT=T_2-T_1$. An uncertainty $\delta_{dp}$ of the estimated saturation pressure difference dP tends to be related to uncertainty in the coefficients $a_T$ and $b_T$ and may therefore be quantified using a covariance matrix, for example, as follows:

$$\delta_{dP}^2 \approx x \, cov(a_T, b_T) x^T \quad (3)$$

where $x=[dT, 2\ T_1 dT+dT^2]$ and $x^T$ represents the transpose of x.

With continued reference to FIGS. 3 and 6, the saturation pressure decrement dP and its relative uncertainty $\delta_{dp}$ may be estimated, for example, using Equations 2 and 3. Thus the saturation pressure at $T_1$ may be estimated, for example, as follows:

$$P_b(T_1)=P-dP \pm \delta_{dP} \quad (4)$$

where $P_b$ ($T_1$) represents the saturation pressure at temperature $T_1$ ($P_b$ in FIG. 6) and P represents the pressure in the flowline (also $P'_b$ in FIG. 6).

Figure 7:
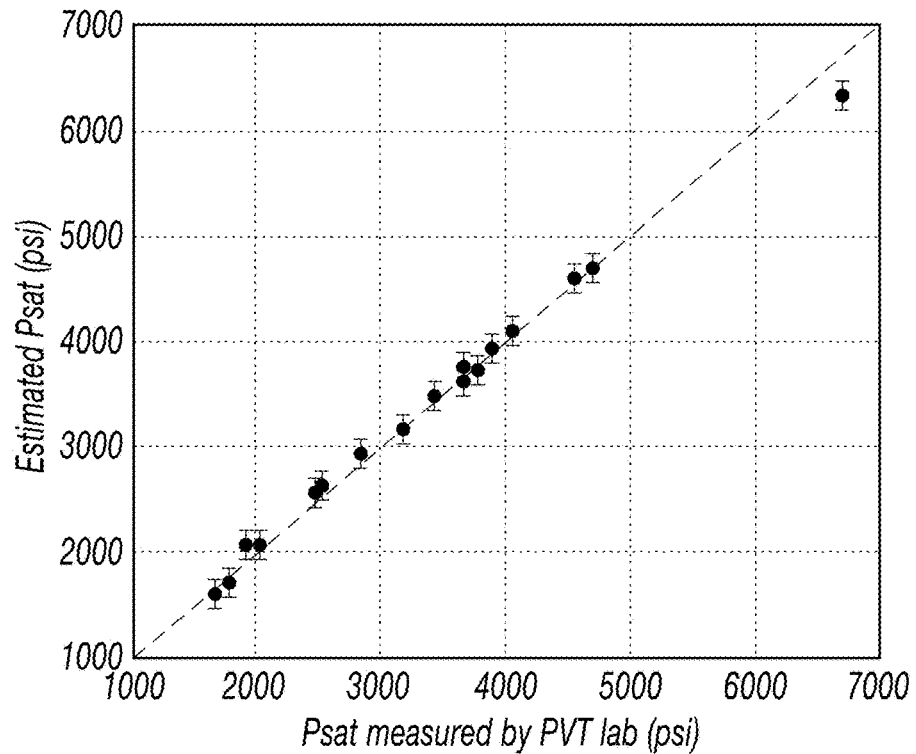
FIG. 7 depicts a plot of example estimated saturation pressures versus laboratory saturation pressure measurements using various types of crude oils.

FIG. 7 depicts a plot of the saturation pressure estimated via Equation 4 versus the saturation pressure derived from laboratory measurements using various types of crude oils having saturation pressures that range from about 2,000 to about 6700 psi at 75 degrees C. and single-stage flash gas oil ratios ranging from about 160 to 3,000 standard cubic feet per stock tank barrel (scf/stb). In this example, the saturation pressure at $T_2$ was measured in the laboratory and the saturation pressure at $T_1$ was estimated using the methodology described above where a difference between the flowline temperature $T_1$ and temperature after heating $T_2$ was arbitrarily set to 50 degrees (such that dT=50 degrees). Note the excellent fit between the saturation pressure values estimated using Equation 4 and those obtained via laboratory measurements. FIG. 7 also depicts the uncertainties associated with each estimate computed according to Equation 3.

Figure 8:
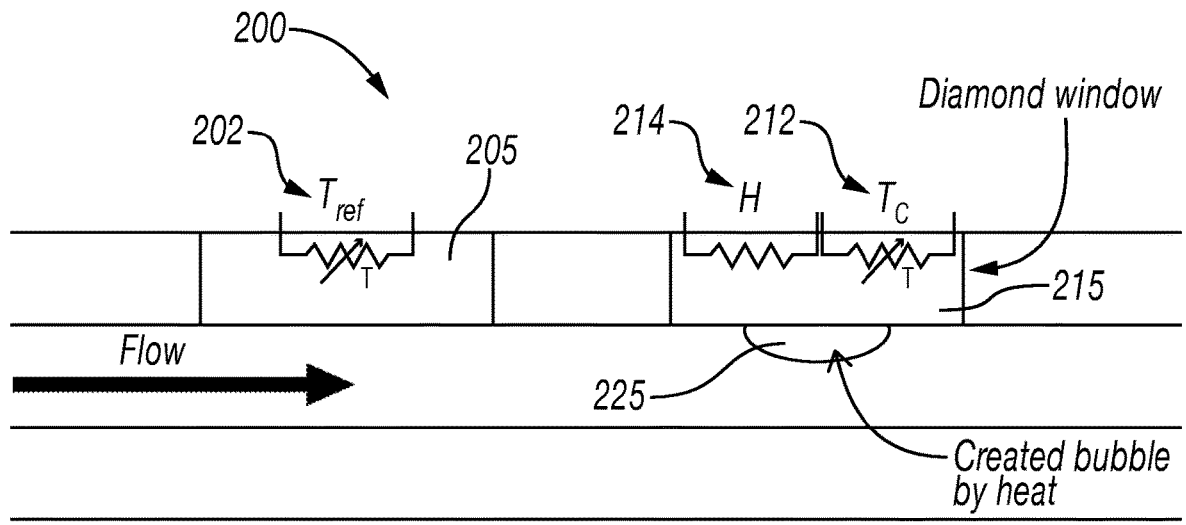
FIG. 8 depicts one example embodiment of the bubble sensor shown on FIG. 2.

FIG. 8 depicts one example embodiment of the bubble sensor 200 described above with respect to FIG. 2. As depicted, the sensor 200 may be deployed in/on the flowline 110. In the depicted embodiment, the bubble sensor includes first and second temperature sensors 202 and 212 and a heater element 214. Temperature sensor 202 (also referred to as a reference temperature sensor) is deployed upstream of temperature sensor 212 and heater element 214 and is optional. In the depicted embodiment, temperature sensor 212 and heater element 214 are packaged as a single element 210. Suitable sensors and heating elements are disclosed in U.S. Pat. No. 8,616,282, which is incorporated by reference in its entirety herein.

In a preferred embodiment, sensors 202, 212, and element 214 may be deployed, for example, on corresponding diamond substrates 205 and 215. The use of a diamond substrate may be advantageous owing to the high thermal conductivity of diamond and its mechanical strength against high pressure and high temperature fluids in the flowline.

During a formation fluid sampling operation, sensor 202 may be used to measure the reference temperature of the fluid in the flowline. Heating and sensing by heater 214 and sensor 212 may be carried out simultaneously. A suitable heating sequence may make use of AC, DC, and/or pulsed electrical current (the disclosed embodiments are not limited in this regard). The temperature reading $T_c$ at sensor 212 will be understood to depend on the local thermal properties of the system, including the thermal conductivity and heat capacity of the flowline fluid, and the fluid flow rate. Upon bubble formation (when the temperature has increased sufficiently to form a bubble in the flowline, for example, as depicted at 225 and as described above with respect to FIG. 6), the heat transfer coefficient between the diamond substrate and the flowline fluid tends to decrease, thereby resulting in an increase in $T_c$. Bubble formation may thus be readily detected via a measured temperature profile at sensor 212.

In alternative embodiments, the sampling tool 100 may further (or alternatively) include a thermoelectric cooling element for cooling the formation fluid in the flowline. When sampling dense phase formation fluids, such cooling may induce bubble formation in the flowline (as the fluid cools from the dense phase regime into the two phase regime) and thereby enable the saturation pressure to be determined in a manner similar to that described above.

Figure 9:
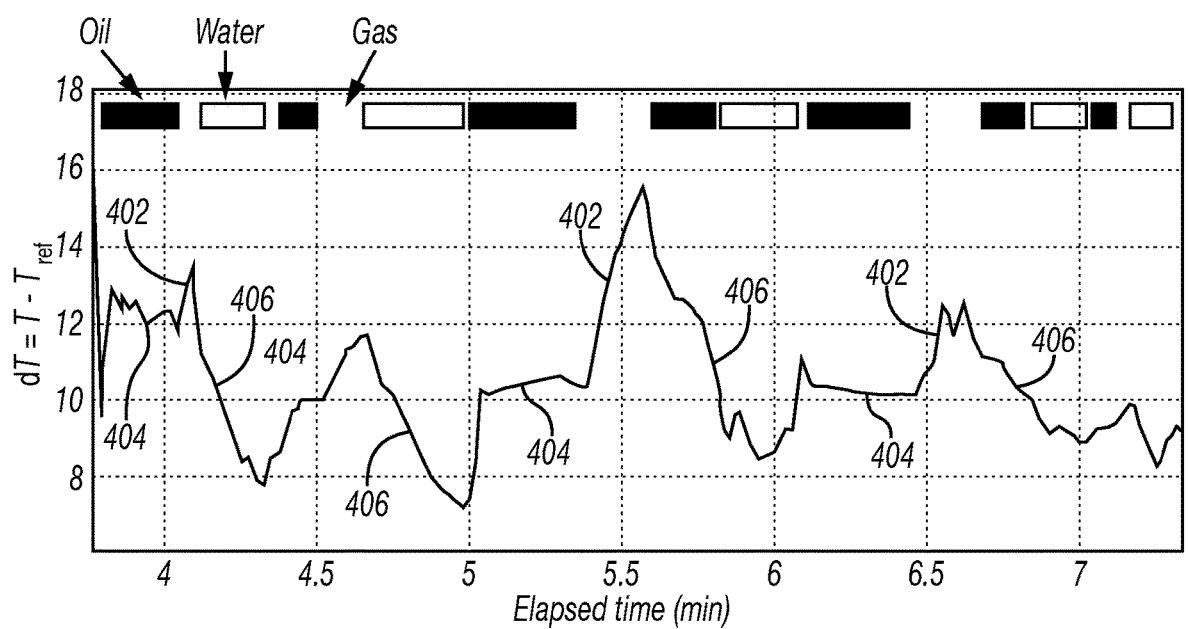
FIG. 9 plots one example of measured temperature sensor responses to different fluid types (oil, gas, and water) in a flowline.

FIG. 9 plots one example of temperature sensor responses to different fluid types (oil, gas, and water) in a flowline. The temperature difference $dT=T_c-T_{ref}$ (equivalently $dT=T_2-T_1$ as shown on FIG. 6 where $T_2=T_c$ and $T_1=T_{ref}$) is plotted versus time for an example sensor arrangement of the type depicted on FIG. 8. The fluid type (oil, gas, or water) is indicated at the top of the plot. In this example constant heat is applied to the flowing fluid. The temperature difference dT responds differently depending on the fluid type. While not wishing to be bound by theory, this effect is likely attributable to the heat transfer coefficients of the fluids which are related to the different thermal conductivity and heat capacity thereof. Note that the temperature difference dT tends to (i) increase (e.g., at 402) when the fluid is a gas, (ii) remain approximately constant (e.g., at 404) when the fluid is oil, and (iii) decrease when the fluid is water (e.g., at 406). By evaluating the temperature profile (e.g., a trend of dT with time) the sensor 200 may be capable of detecting the presence of gas bubbles in the above described methods.

Figure 10:
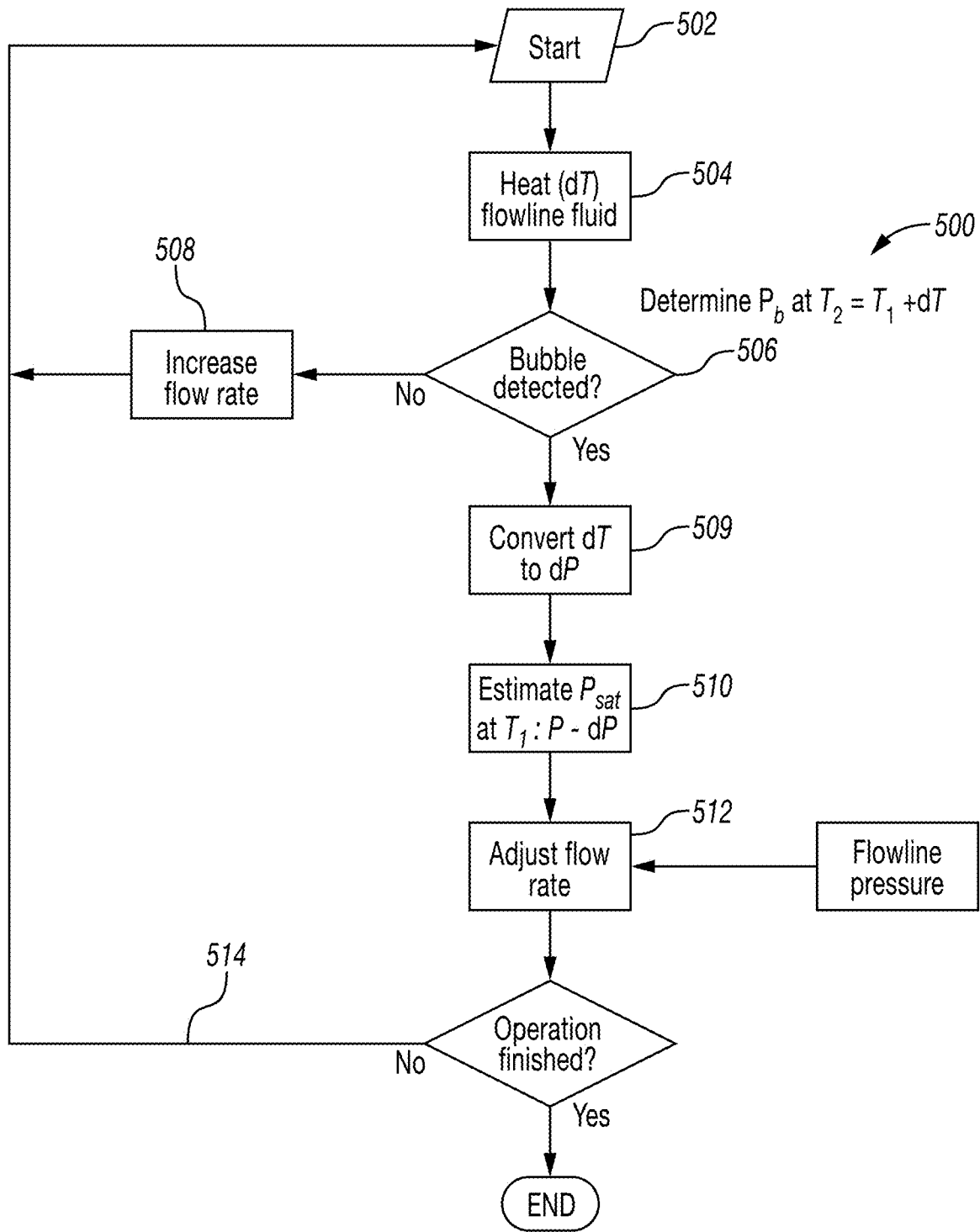
FIG. 10 depicts a flow chart of another disclosed method embodiment.

FIG. 10 depicts a flow chart of another disclosed method embodiment 500 for obtaining a formation fluid sample. Method 500 is similar to method 300 in that formation fluid is drawn/pumped into the flowline of a downhole sampling tool (e.g., flowline 110 of sampling tool 100 depicted on FIGS. 1 and 2) at 502. As described above, the contamination level in the fluid may be changing continuously while pumping in 502. At 504, the bubble sensor 200 heats the flowline fluid (e.g., by dT) at 504. The sensor simultaneously measures temperature $T_c$ (and optionally $T_{ref}$) at 506 to detect bubble formation. If no bubble is detected (e.g., in a predetermined time window), the flow rate may be incrementally increased at 508. If a bubble is detected at 506 (e.g., via a rapidly increasing dT as described above with respect to FIG. 9), then the saturation pressure $P_b$ and its uncertainty may be computed at 509 and 510, for example, as described above with respect to Equations 2-4. The flow rate may then be adjusted (e.g., downward) at 512 to avoid bubble formation based on the computed saturation pressure $P_b$ (so as to avoid crossing the phase boundary while pumping). The process may continue (as indicated at 514) until a suitable formation fluid sample has been acquired.

Although a flowline saturation pressure measurement method and apparatus and certain advantages thereof have been described in detail, it should be understood that various changes, substitutions and alternations can be made herein without departing from the spirit and scope of the disclosure as defined by the appended claims.

What is claimed is:

1. A method for sampling a downhole formation fluid, the method comprising:
   (a) pumping formation fluid into a flowline of a downhole sampling tool, wherein the flowline is deployed between a fluid inlet probe and a pump;
   (b) heating formation fluid in the flowline while pumping in (a);
   (c) measuring a temperature of the formation fluid in the flowline while heating in (b);
   (d) evaluating said temperature estimates in (c) to detect whether or not a gas bubble has formed in the flowline;
   (e) increasing a pumping rate in (a) when a gas bubble is not detected in (d);
   (f) determining a temperature indicative of bubble formation when a bubble is detected in (d) and processing a flowline pressure, a reference temperature, the temperature indicative of bubble formation, and a formation fluid model to compute the saturation pressure of the formation fluid at the reference temperature; and
   (f) reducing the pumping rate in (a) when the saturation pressure computed in (e) is greater than the flowline pressure.

2. The method of claim 1, wherein the gas bubble is detected in (d) by evaluating a time based change of a difference between said temperature estimates and the reference temperature.

3. The method of claim 2, wherein the gas bubble is detected when the difference between said temperature estimates and the reference temperature increases with time.

4. A downhole formation fluid sampling tool comprising:
   a fluid flowline deployed between a fluid inlet probe and a pump; and
   a bubble sensor deployed in the fluid flowline, the bubble sensor including a heating element and a temperature sensor deployed on a common substrate.

5. The sampling tool of claim 4, further comprising a reference temperature sensor deployed in the fluid flowline upstream of the bubble sensor.

6. The sampling tool of claim 4, wherein the heating element and the temperature sensor are deployed on a common diamond substrate.

7. The sampling tool of claim 4, further comprising a controller configured to:
   (i) cause the pump to pump formation fluid through the flowline;
   (ii) measure a saturation pressure of the formation fluid in the flowline while pumping in (i); and
   (iii) adjust a rate of pumping in (i) such that a fluid pressure in the flowline remains within a predetermined threshold above the saturation pressure measured computed in (ii).

8. The sampling tool of claim 4, further comprising a controller configured to:
   (i) cause the pump to pump formation fluid through the flowline;
   (ii) cause the heating element to heat the formation fluid in the flowline while pumping in (i);

(iii) cause the temperature sensor to measure a temperature of the formation fluid in the flowline while heating in (ii);
(iv) evaluate said temperature measurements in (iii) to determine a temperature indicative of bubble formation in the flowline;
(v) process a flowline pressure, a reference temperature, the temperature indicative of bubble formation, and a formation fluid model to compute a saturation pressure of the formation fluid at the reference temperature; and
(vi) adjust a rate of pumping in (i) such that a fluid pressure in the flowline remains within a predetermined threshold above the saturation pressure computed in (v).

* * * * *